US009958391B2

(12) United States Patent
Drumm et al.

(10) Patent No.: US 9,958,391 B2
(45) Date of Patent: May 1, 2018

(54) LIGHTING DEVICE (71) Applicant: OSRAM GmbH, Munich (DE)

(72) Inventors: Jan Oliver Drumm, Regensburg (DE); Jens Richter, Deuerling (DE)

(73) Assignee: OSRAM GMBH, Munich (DE)

( * ) Notice: Subject to any disclaimer, the term of this patent is extended or adjusted under 35 U.S.C. 154(b) by 0 days. days.

(21) Appl. No.: 15/496,011

(22) Filed: Apr. 25, 2017

(65) Prior Publication Data

US 2017/0322155 A1 Nov. 9, 2017

(30) Foreign Application Priority Data

May 4, 2016 (DE) .......................... 10 2016 207 757

(51) Int. Cl.
*G01N 21/64* (2006.01)
*B60Q 11/00* (2006.01)
*F21S 8/10* (2006.01)
*F21V 9/16* (2006.01)
*F21Y 115/30* (2016.01)

(52) U.S. Cl.
CPC ....... *G01N 21/6445* (2013.01); *B60Q 11/005* (2013.01); *F21S 48/1145* (2013.01); *F21V 9/16* (2013.01); *F21Y 2115/30* (2016.08)

(58) Field of Classification Search
CPC ...... B60Q 11/005; F21S 48/1145; F21V 9/16; F21Y 2115/30; G01N 21/6445
See application file for complete search history.

(56) References Cited

U.S. PATENT DOCUMENTS

| | | | |
|---|---|---|---|
| 8,395,312 B2 * | 3/2013 | Hum | H01L 25/0753 313/500 |
| 9,159,885 B2 * | 10/2015 | Ouderkirk | H01L 25/0753 |
| 2011/0044046 A1 * | 2/2011 | Abu-Ageel | F21K 9/00 362/259 |
| 2015/0377695 A1 * | 12/2015 | Chang | G01J 1/0252 250/208.2 |

(Continued)

FOREIGN PATENT DOCUMENTS

| DE | 102012220481 A1 | 5/2014 |
|---|---|---|
| DE | 202015001682 U1 | 3/2015 |

(Continued)

OTHER PUBLICATIONS

German Search Report based on application No. 10 2016 207 757.0 (7 pages) dated Apr. 20, 2017 (Reference Purpose Only).

*Primary Examiner* — Marcus Taningco
(74) *Attorney, Agent, or Firm* — Viering, Jentschura & Partner mbB (57) ABSTRACT

In various embodiments, a lighting device is provided. The lighting device includes a phosphor volume for at least partial wavelength conversion of primary light into secondary light, a primary light semiconductor light source for irradiating the phosphor volume with primary light, a measurement light generating arrangement for generating measurement light having a spectral composition outside the primary light and the secondary light, a measurement light detector sensitive to the measurement light, and a measurement light filter, which is fixedly connected to the phosphor volume and is optically arranged between the measurement light generating arrangement and the measurement light detector.

15 Claims, 3 Drawing Sheets

(56) References Cited

U.S. PATENT DOCUMENTS

2017/0240094 A1* 8/2017 Kunecke .............. B60Q 1/0023

FOREIGN PATENT DOCUMENTS

| DE | 102014202943 A1 | 8/2015 |
| DE | 102014212370 A1 | 12/2015 |
| WO | 2014072226 A1 | 5/2014 |
| WO | 2015124428 A1 | 8/2015 |

* cited by examiner

LIGHTING DEVICE

CROSS-REFERENCE TO RELATED APPLICATION

This application claims priority to German Patent Application Serial No. 10 2016 207 757.0, which was filed May 4, 2016, and is incorporated herein by reference in its entirety.

TECHNICAL FIELD

Various embodiments relate generally to a lighting device, including a phosphor volume for at least partial wavelength conversion of primary light into secondary light, a primary light semiconductor light source for irradiating the phosphor volume with primary light, a measurement light generating arrangement for generating measurement light having a spectral composition outside the primary light and the secondary light, and a measurement light detector sensitive to the measurement light. Various embodiments are applicable e.g. to vehicle illumination devices, e.g. based on the LARP principle, e.g. to headlights.

BACKGROUND

In LARP ("Laser Activated Remote Phosphor") arrangements, at least one laser generates primary light that is converted at least partly into secondary light of a different wavelength by means of a wavelength-converting phosphor volume. The mixed light resulting from the secondary light and, if appropriate, a portion of the primary light that is not converted but is scattered by the phosphor volume can be used as useful light. By way of example, white useful light can be generated from a mixture of blue primary light and yellow secondary light. If, in the case of a transmissive arrangement, the phosphor volume is damaged in the region of the incident primary light beam, disadvantageously coherent primary light can pass through the phosphor volume and possibly not comply with predefined limit values with regard to eye safety. On account of the type of stimulating source (laser), often even a small degree of damage to the phosphor volume should be rated as critical for the purposes of eye safety. When a case of damage is identified, the laser generating the primary light can be deactivated or the primary light can be switched off.

In order to be able to identify damage to the phosphor volume, it is known to employ a relationship of exciting and transmitted power of the primary light and also a power of the secondary light. If, in this case, with constant exciting power, the transmitted power of the primary light increases and the power of the secondary light decreases, damage to the phosphor volume is assumed. One disadvantage of this method consists in the high outlay for the measurement set-up, e.g. owing to a high number of light sensors required. Moreover, the calibration, measurement data recording and the measurement data evaluation are complex. Furthermore, a higher reliability of the detection of the fault case or case of damage is desired. Particularly a detection when there is only a small change in the powers is not always possible without errors, since a laser power in the spectral range of the primary light is transmitted in normal operation as well.

DE 20 2015 001 682 U1 discloses an illumination device for a vehicle including a laser diode arrangement, a light wavelength conversion element for wavelength conversion of the light generated by the laser diode arrangement, and also a safety device for measuring a fault case of the light wavelength conversion element, wherein the safety device comprises at least one signal generator and at least one signal receiver for transmitting and receiving measurement radiation, wherein the at least one signal generator and the at least one signal receiver are arranged on different sides of the light wavelength conversion element, such that measurement radiation from the at least one signal generator penetrates through the light wavelength conversion element.

SUMMARY

In various embodiments, a lighting device is provided. The lighting device includes a phosphor volume for at least partial wavelength conversion of primary light into secondary light, a primary light semiconductor light source for irradiating the phosphor volume with primary light, a measurement light generating arrangement for generating measurement light having a spectral composition outside the primary light and the secondary light, a measurement light detector sensitive to the measurement light, and a measurement light filter, which is fixedly connected to the phosphor volume and is optically arranged between the measurement light generating arrangement and the measurement light detector.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

Various embodiments at least partly overcome the disadvantages of the prior art and, for example, to provide an improved possibility for ascertaining damage to a phosphor body.

Various embodiments provide a lighting device, including a phosphor volume for at least partial wavelength conversion of primary light into secondary light, a semiconductor light source for irradiating the phosphor volume with primary light, a measurement light generating arrangement for generating measurement light having a spectral composition outside the primary light and the secondary light, a measurement light detector sensitive to the measurement light, and a measurement light filter, which is fixedly connected to the phosphor volume and is optically arranged between the measurement light generating arrangement and the measurement light detector.

The fact that the phosphor volume is fixedly connected to the measurement light filter (i.e. an optical filter that blocks or inhibits the measurement light) has the effect that the measurement light filter is likewise damaged in the event of local damage to the phosphor volume. If cracks or ablations form in the phosphor volume, for example, they will continue into the filter and damage the filter as well. Consequently, in the non-damaged state of the phosphor volume e.g. only very little or practically no measurement light can pass to the measurement light detector (i.e. to a light detector sensitive to the measurement light) because the likewise non-damaged measurement light filter is arranged optically between the measurement light generating arrangement and the measurement light detector. By contrast, in the case of damage, at the location of the damage the measurement light can pass through the measurement light filter and be incident in the measurement light detector. With the resultant detection of the measurement light, underlying damage to the phosphor volume can be identified particularly accurately and it is possible to take countermeasures in order to avoid eye damage.

The use of the measurement light filter also enables a particularly accurate and early identification in particular even of relatively minor damage, since a basic level of the measurement light that is incident in the measurement light sensor in the undamaged state of the phosphor volume and thus of the filter is very low. Without use of the measurement light filter, by contrast, the basic level would be appreciably higher, since the measurement light can pass through the phosphor volume—which acts as a scattering body for the non-converted primary light and for the measurement light. By means of the measurement light filter, it is thus possible to considerably reduce "basic noise" of measurement light incident in the light detector or to considerably improve a signal-to-noise ratio. As a result in turn a fault case or case of damage can be reliably identified solely by observation or monitoring of the measurement light. Small changes in the measurement light at the measurement light detector are not superimposed by potentially significantly greater fluctuations of the useful light.

Moreover, the effect may be afforded that a dynamic range of the measurement set-up and thus a reliability of the detection of the case of damage are determined solely by the possibly still remaining low transmittance of the measurement light filter in the stop band, by noise of the light detector and possibly by signal processing noise. It is thus possible for critical damage to the phosphor volume in the sense of eye safety to be detected particularly safely.

On account of the simplified set-up in comparison with the prior art, the outlay of the lighting device is furthermore reduced, since the measurement set-up and the damage identification based thereon can be considered independently of the optical path of the primary light and of the secondary light. This is advantageous e.g. with regard to a calibration of the lighting device.

The lighting device may be an illumination device. It may emit mixed light composed of the primary light and the secondary light as useful light, e.g. white useful light, the color locus of which may lie in the ECE white field standardized for vehicle headlights.

The phosphor volume includes at least one phosphor suitable for converting incident primary light at least partly into secondary light of a different wavelength. If a plurality of phosphors are present, they may generate secondary light portions having mutually different wavelengths. The wavelength of the secondary light may be longer (so-called "down conversion") or shorter (so-called "up conversion"), than the wavelength of the primary light. By way of example, blue primary light may be converted into green, yellow, orange or red secondary light by means of a phosphor. In the case of only partial wavelength conversion, a mixture of secondary light and non-converted primary light is emitted by the phosphor volume, which mixture may serve as useful light. By way of example, white useful light may be generated from a mixture of blue, non-converted primary light and yellow secondary light. However, full conversion is also possible, wherein the primary light is either no longer present in the useful light or present therein only in a negligible proportion. A degree of conversion is dependent, for example, on a thickness and/or a phosphor concentration of the phosphor. If a plurality of phosphors are present, secondary light portions of different spectral compositions may be generated from the primary light, e.g. yellow and red secondary light. The red secondary light may be used for example to impart a warmer hue to the useful light, e.g. so-called "warm-white". If a plurality of phosphors are present, at least one phosphor may be suitable for subjecting secondary light to wavelength conversion again, e.g. green secondary light into red secondary light. Such a light that has been subjected to wavelength conversion again from a secondary light may also be referred to as "tertiary light".

At least one semiconductor light source for irradiating the phosphor volume with primary light ("primary light semiconductor light source") may be a laser, e.g. a laser diode. The primary light emitted thereby may be referred to as pump light. Alternatively or additionally, at least one semiconductor light source may be a light emitting diode. At least one optical element, e.g. at least one reflector, at least one lens and/or at least one diffuser, etc., may be present in an optical path between at least one primary light semiconductor light source and at least one phosphor volume.

That surface region of the phosphor volume which can be irradiated by the primary light may also be referred to as its "primary light irradiation surface". When the primary light source is switched on, a luminous spot forms there.

The different, e.g. disjoint, spectral composition of the measurement light in comparison with the primary light and with the secondary light serves to prevent interference or optical crosstorque. The measurement light may have e.g. a different wavelength than the primary light and the secondary light. In one development, the wavelength of the measurement light is greater than the wavelength of the primary light, e.g. also greater than the wavelength of the (at least one) secondary light. In this regard, the measurement light may be prevented particularly reliably from being subjected to wavelength conversion by the phosphor volume. By way of example, the primary light may be blue light, the secondary light may be yellow light and the measurement light may be red light. Alternatively, e.g. the secondary light may include yellow light and red light, while the measurement light is infrared light.

In one development, the wavelength of the measurement light is less than the wavelength of the primary light, e.g. also less than the wavelength of the (at least one) secondary light. In this regard, the measurement light may be prevented particularly reliably from being subjected to wavelength conversion by the phosphor volume. By way of example, the primary light may be blue light, the secondary light may be yellow light and the measurement light may be ultraviolet light.

The measurement light filter e.g. has a low transmittance for the measurement light of 15% or less, e.g. of 10% or less, e.g. of 5% or less, e.g. of 3% or less, e.g. of 1% or less. The measurement light filter e.g. has a high transmittance for the primary light and/or the secondary light of 85% or more, e.g.

of 90% or more, e.g. of 95% or more, e.g. of 98% or more, e.g. of 99% or more. The measurement light filter may also be referred to as "measurement light blocking filter".

If the measurement light passes with a measurable intensity through the measurement light filter, the measurement light detector can identify whether or not the measurement light generating arrangement is switched on or activated. In this regard, if appropriate, it is possible to dispense with a further (reference) measurement light filter for directly sensing the measurement light. For this case it may be provided for the measurement light filter to have a transmittance of between 5% and 20%, e.g. between 10% and 15%.

The measurement light detector may be insensitive at least to the primary light; it may be sensitive to the secondary light in this case. In one development, the measurement light detector is sensitive only to the measurement light, i.e. neither to the primary light nor to secondary light. The measurement light detector may be or include for example a light-sensitive diode, if appropriate with an upstream spectral filter.

The lighting device may include e.g. a plurality of phosphor volumes, a plurality of primary light semiconductor light sources, a plurality of measurement light generating arrangements, a plurality of measurement light detectors and/or a plurality of measurement light filters.

The lighting device may be a module downstream of which there is disposed at least one further optical unit, e.g. coupling-out optical unit for coupling out useful light.

The lighting device may include an evaluation unit or be coupled to an evaluation unit that is configured to evaluate the measurement data of the measurement light detector and to ascertain damage to the phosphor volume. The damage may be ascertained e.g. by a signal rise and/or by a signal threshold being exceeded. The lighting device—e.g. the evaluation unit thereof—may additionally be configured to dim or switch off the primary light in the event of damage being ascertained.

In one embodiment, the measurement light filter is a filter layer applied to the phosphor volume. By virtue of its small thickness the filter layer enables a particularly high transmittance for the primary light and/or for the secondary light. The filter layer may include one layer or a plurality of layers.

For example for the case where the measurement light filter is a filter layer applied to the phosphor volume, in one embodiment, a thickness of the measurement light filter is at least two times smaller than a thickness of the phosphor volume, e.g. at least five times smaller. This affords the effect that a defect in the phosphor volume (e.g. cracking and/or partial ablation, etc. on account of aging or prior damage, for example) leads particularly simply and noticeably to a defect of the measurement light filter.

In one development, a layer thickness of the measurement light filter is five micrometers or less. In another development, a thickness of the phosphor volume lies in a range of between 10 micrometers and 300 micrometers.

In another embodiment, the measurement light filter has been produced on the phosphor volume. A particularly direct and fixed connection to the phosphor volume is achieved as a result. This in turn particularly reliably has the effect that damage to the phosphor volume leads to corresponding damage to the measurement light filter and e.g. not just to detachment of the filter layer from the phosphor volume. In one development, the measurement light filter—if appropriate after prior processes such as, for example, plasma cleaning and polishing of a surface of the phosphor volume—has been produced by physical vapor deposition (PVD, such as, for example, sputtering or general vapor deposition), chemical vapor deposition (CVD).

Alternatively, the measurement light filter may have been produced separately and then attached to the phosphor volume, e.g. may have been adhesively bonded thereto.

In a further embodiment, the phosphor volume is a ceramic phosphor body. A ceramic phosphor body is particularly durable mechanically and also thermally. As a result, it is particularly suitable also as a substrate for applying the measurement light filter.

If the ceramic phosphor body is in sheet form or laminar, the measurement light filter may be applied as a filter layer e.g. on one at least flat side of the ceramic phosphor body. The filter layer may cover the entire flat side or only part of the flat side.

The phosphor volume may alternatively include phosphor embedded into light-transmissive matrix material, e.g. one or a plurality of phosphor powders. Such a phosphor body may likewise be in sheet form or laminar having two flat sides which face away from one another and which need not necessarily be embodied as parallel and regularly planar.

A flat side which can be irradiated with the primary light is also referred to as "irradiation side". A flat side from which the useful light can be emitted is also referred to as "light emission side". In the case of a transmissive arrangement, the irradiation side and the light emission side are different flat sides. In the case of a reflective arrangement, the irradiation side and the light emission side are the same flat sides. The flat sides may be plane or curved.

In yet another embodiment, the measurement light filter is a filter that reflects the measurement light. By contrast, the primary light and the secondary light are not reflected, but rather transmitted. Such a measurement light filter has the effect that it has a high effectiveness and does not heat up appreciably on account of the incident measurement light.

The reflective measurement light filter may be e.g. a dielectric filter constructed as a layer stack of dielectric layers having predefined thicknesses and alternating refractive indexes. The reflective measurement light filter may be e.g. an interference filter or interference mirror. The reflective measurement light filter may be a Bragg mirror having a stop band containing the spectrum of the measurement light. The reflective measurement light filter may be e.g. a dichroic filter if the measurement light has a spectral range having only longer or only shorter wavelengths than the spectral ranges of the primary light and of the secondary light. A dichroic filter can be produced in a particularly simple manner. However, the reflective measurement light filter may also be a trichroic filter if the measurement light has a spectral range situated between the spectral ranges of the primary light and of the secondary light, etc. Possible interference filters are e.g. layer stacks of $TiO_2/SiO_2$, $Ta_2O_5/SiO_2$ or $Nb_2O_5/SiO_2$. The layer stacks may contain e.g. layer numbers of up to 100 layers.

In one embodiment, moreover, the measurement light filter is a filter that absorbs the measurement light. Such a measurement light filter may act on account of its material absorption (e.g. band edge absorption or intraband absorption). By way of example, indium titanium oxide (ITO) is one possible material of such a measurement light filter. ITO is a ternary material system with a band gap at 4 eV (i.e. in the deep UV). ITO is transparent in the visible spectral range. Energetically above the band gap, ITO is nontransparent on account of the absorption property of the band gap. In the IR range at approximately 1600 nm, ITO becomes nontransparent again. The intraband absorption and/or the interband absorption of charge carriers in the conduction band take(s) effect here. By varying the material composition (in particular a proportion of indium with respect to tin) and process parameters during production, it is possible to vary the absorption edges. Further possible materials include e.g. indium cadmium oxide, aluminum zinc oxide (AZO), gallium zinc oxide (GZO) or indium zinc oxide (IZO). Generally, e.g. a multiplicity of III-V and II-VI semiconductor compounds and the oxides thereof are also appropriate, e.g. $In0.2Ga0.8N$ or $TiO_2$.

The measurement light filter may also be a filter that both reflects and absorbs, e.g. in order to obtain a particularly thin filter that is further improved for the transmission of the primary light and secondary light and also for the blocking effect for the measurement light.

In one embodiment, moreover, the measurement light generating arrangement includes at least one semiconductor light source for irradiating the phosphor volume with the measurement light ("measurement light semiconductor light source").

The measurement light semiconductor light source may be a laser, e.g. a laser diode. Alternatively or additionally, at least one semiconductor light source may be a light emitting diode. At least one optical element, e.g. at least one reflector, at least one lens and/or at least one diffusor, etc., may be present in an optical path between the measurement light semiconductor light source and the phosphor volume.

In one development, the measurement light irradiation surface determined by the impinging measurement light corresponds to the primary light irradiation surface determined by the primary light or includes the primary light irradiation surface. In this regard, it is possible to ensure particularly reliably that at the phosphor volume no region irradiated by the primary light is present which is not also monitored by the measurement light.

In an alternative or additional embodiment, the measurement light generating arrangement includes the phosphor volume, which is then additionally designed for converting the primary light and/or the secondary light into the measurement light. The measurement light is thus only generated within the phosphor volume when the phosphor volume is irradiated by the primary light. The measurement light generating arrangement may thus also include the primary light semiconductor light source. By contrast, a dedicated measurement light semiconductor light source may be dispensed with or a measurement light semiconductor light source having a lower power may be used. The measurement light may be ("measurement") secondary light or ("measurement") tertiary light, etc. that is different than a useful light portion. The phosphor volume may include or be e.g. $Eu3+:LuAG$, IR quantum dots, etc.

In another alternative or additional embodiment, the measurement light generating arrangement includes a phosphor layer present e.g. between the phosphor volume (which itself does not generate measurement light) and the measurement light filter and serves for converting primary light and/or secondary light into the measurement light. The measurement light is thus only generated between the phosphor volume and the measurement light filter. In this regard, too, a measurement light semiconductor light source may be dispensed with or a measurement light semiconductor light source having a lower power may be used. The phosphor layer, too, may include $Eu3+:LuAG$, IR quantum dots, etc.

In one development, the measurement light is light that is invisible to human beings, e.g. UV light or IR light. Light that is invisible to human beings as the measurement light affords the effect that the measurement light is not perceived as admixture with the useful light by an observer. For example the use of IR light affords the effect that it is not suitable for generating secondary light in the visible range. This increases a selection of possible phosphors.

In one development that may be provided for ensuring a high signal-to-noise (SNR) ratio of the measurement light detector—e.g. for IR light as the measurement light—a further or additional measurement light filter is disposed upstream of the measurement light detector, said filter transmitting only the measurement light, but blocking useful light and extraneous light. The further measurement light filter may be situated for example directly upstream of a measurement window of the measurement light detector. It may be embodied e.g. as a suitably coated cover glass. Said further measurement light filter may structurally or functionally correspond to the measurement light filter fixedly connected to the phosphor volume or may be a measurement light filter that is structured differently or acts differently.

IR measurement light may have e.g. a wavelength of more than 750 nm, e.g. of more than 1600 nm. UV measurement light may have e.g. a wavelength of less than 410 nm.

In another embodiment, the measurement light is pulsed measurement light. This allows an even finer detection of the measurement light and thus an even more accurate identification of damage. In various embodiments, the measurement light can thus be distinguished particularly accurately from constant or only slowly changing extraneous light, e.g. ambient light. Alternatively or additionally, the measurement light may also have an impressed modulation frequency or code sequence.

In one embodiment, moreover, the measurement light generating arrangement and the measurement light detector are situated in a transmissive arrangement with respect to the measurement light filter. In this regard, damage can be identified particularly reliably with little outlay. In the case of the transmissive arrangement, the primary light semiconductor light source and the measurement light detector are situated on different sides of the measurement light filter. In the non-damaged state of the measurement light filter, the measurement light does not pass to the measurement light sensor. In the event of damage to the measurement light filter, the luminous flux of the measurement light that is incident in the measurement light detector thus increases.

In one development, the measurement light detector is situated in a direct optical path of the measurement light, as a result of which, in the event of damage to the measurement light filter, a particularly high luminous flux and thus a particularly sensitive ascertainment of the damage can be attained. A direct optical path of the measurement light is understood to mean, for example, an optical path of the measurement light in the absence of the phosphor volume and the measurement light filter connected thereto. In this development, the measurement light passes completely from the measurement light semiconductor light source into the measurement light detector. If the phosphor volume with the measurement light filter are present, they are introduced in the optical path, and the measurement light filter blocks the measurement light in the non-damaged state.

In an alternative or additional development, the measurement light detector is situated outside a direct optical path of the measurement light, e.g. in an angled manner with respect thereto. In the event of damage to the phosphor volume, it is possible in this case to detect a measurement light passing through the measurement light filter which was previously scattered by the phosphor volume. The measurement light detector may be directed at the phosphor volume e.g. obliquely with respect to the optical path.

In another embodiment, the measurement light generating arrangement and the measurement light detector are situated in a reflective arrangement with respect to the measurement light filter. In this regard, a particularly compact set-up can be attained. In the case of the reflective arrangement, the primary light semiconductor light source and the measurement light detector are situated optically on the same side of the measurement light filter disposed optically therebetween. In the undamaged state of the measurement light filter, the measurement light is reflected from the latter into the measurement light detector and/or scattered into the measurement light detector by a phosphor volume situated optically upstream of the measurement light filter. In the event of damage to the measurement light filter, the luminous flux of the measurement light that is incident in the measurement light detector decreases.

In another embodiment, an additional measurement light detector ("reference measurement light detector") is irradiatable directly by means of the measurement light semiconductor light source. In this regard, an influence of a fluctuation of a luminous flux of the measurement light semiconductor light source can be detected, e.g. in the case of a transmissive arrangement of the measurement light generating arrangement and the ("main") measurement light detector already described above. Thus in turn it is possible to correct the signal of the main measurement light detector used for ascertaining damage, which further increases a detection accuracy. A "direct" irradiation may be understood to mean, for example, an irradiation with the phosphor volume and the measurement light filter being bypassed or omitted or an irradiation with reflection at the measurement light filter.

In another embodiment, the lighting device is designed as a vehicle illumination device. The vehicle illumination device may be a headlight, for example.

The vehicle may be a motor vehicle (e.g. an automobile such as a car, truck, bus, etc. or a motorcycle), a bicycle, a train, a watercraft (e.g. a boat or a ship) or an aircraft (e.g. an airplane or a helicopter).

However, the lighting device may also encompass other fields of application. In this regard, it is possible to use products also in the field of a flashlight or of a forehead lamp with the lighting device.

Various embodiments also provide a vehicle including a lighting device as described above.

Figure 1:
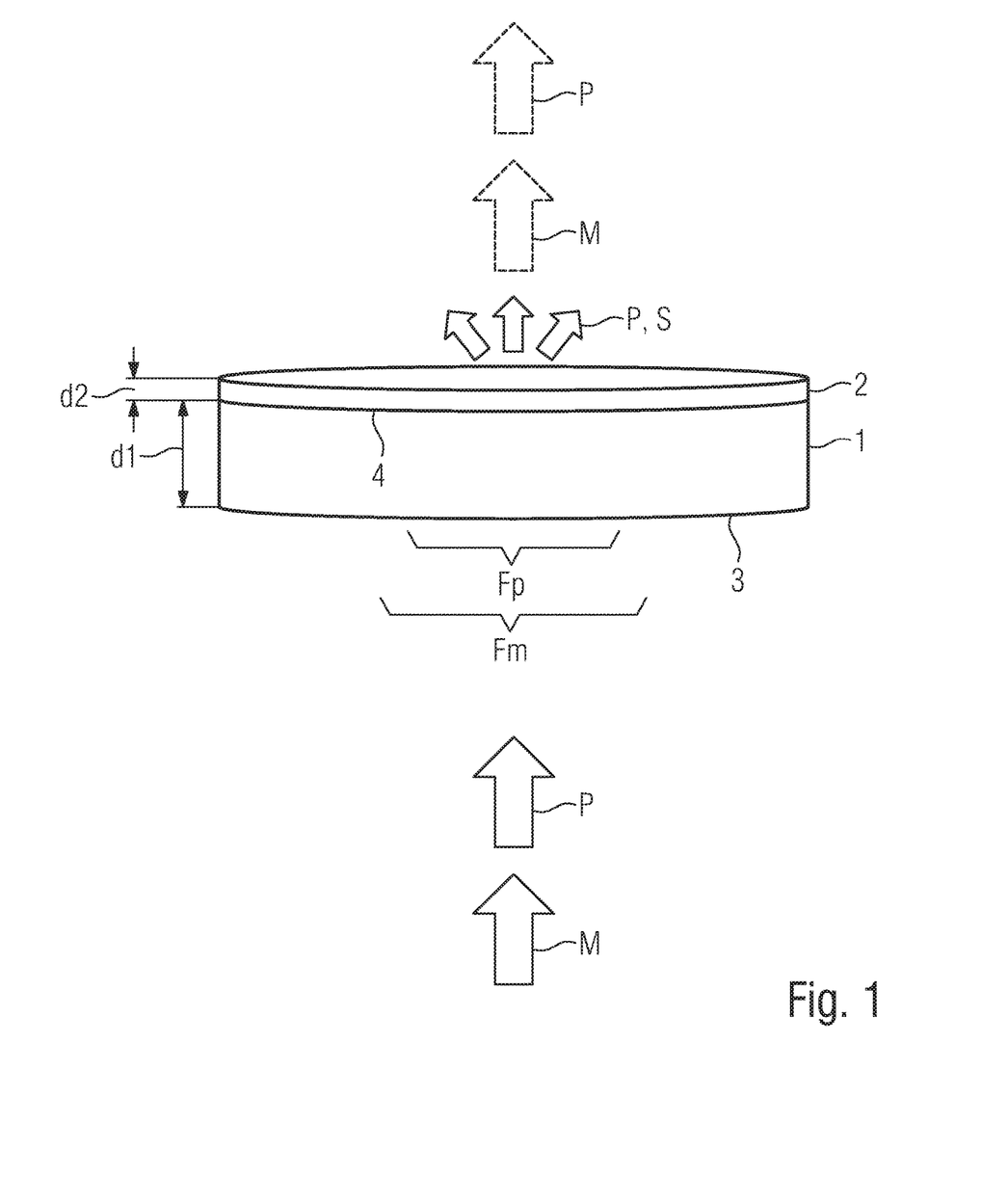
FIG. 1 shows, in an oblique view, a phosphor volume with a measurement light filter fixedly attached thereto.

FIG. 1 shows a phosphor volume in the form of a ceramic phosphor lamina 1 with a measurement light filter 2 fixedly attached thereto on the flat side. The phosphor lamina 1 may have been sintered, for example. The phosphor lamina 1 may be designed as a rare-earth-doped ceramic. Its thickness d1 is 30 micrometers to 300 micrometers, for example.

If—e.g. blue—primary light P is radiated onto a first flat side 3 of the phosphor lamina 1 (specifically onto a primary light irradiation surface Fp), it is converted into—e.g. yellow—secondary light S by the phosphor lamina 1. A large part of the secondary light S and also a large part of the non-converted primary light emerge in a mixed fashion at the other, second flat side 4 of the phosphor lamina 1, the measurement light filter 2 bearing on said second flat side. This mixture of the primary light P and the secondary light S may be used as useful light P, S. Since the phosphor lamina 1 acts as a scattering body for the primary light P and as a Lambertian emitter for the secondary light S, the useful light P, S is not coherent and moreover expanded further than the originally incident primary light P. The measurement light filter 2 is transparent to the primary light P and to the secondary light S (with a transmittance e.g. of more than 90%).

If—e.g. infrared—measurement light M is radiated onto the first flat side 3 of the phosphor lamina 1 (specifically onto a measurement light irradiation surface Fm including the primary light irradiation surface Fp), it is scattered, but not converted, by the phosphor lamina 1. A large part of the measurement light M emerges again at the other, second flat side 4 of the phosphor lamina 1. The measurement light filter 2 is blocking for the measurement light M (with a transmittance of e.g. less than 10%).

For this purpose, the measurement light filter 2 may be a filter layer designed to reflect and/or absorb the measurement light M. It may be designed for example as a dichroic interference filter. The measurement light filter 2 may have been produced fixedly on the second flat side 4 of the phosphor lamina 1 by means of a vapor deposition method, sputtering, etc. Its thickness d2 is e.g. five micrometers or less.

If the phosphor lamina 1 is damaged, e.g. by cracking or chipping, these instances of damage spread to the far thinner measurement light filter 2, which is then correspondingly damaged. On account of its fixed attachment and its small thickness d2, the measurement light filter 2 does not offer any appreciable resistance to the progress of the damage. If damage is present, the primary light P can pass through the phosphor lamina 1 and through the measurement light filter 2 without being scattered there, as indicated by the dotted arrow. Said primary light P may have a high light intensity and possibly lead to eye damage. The measurement light M may also now pass through the measurement light filter 2 at the location of the damage, as indicated by the dotted arrow.

In principle, the measurement light filter 2 may also be attached to the first flat side 3 of the phosphor lamina 1.

The measurement light filter 2 may be attached on one of the flat sides 3, 4 over the whole area, alternatively only partly, e.g. only in the region of the measurement light irradiation surface Fm.

Figure 2:
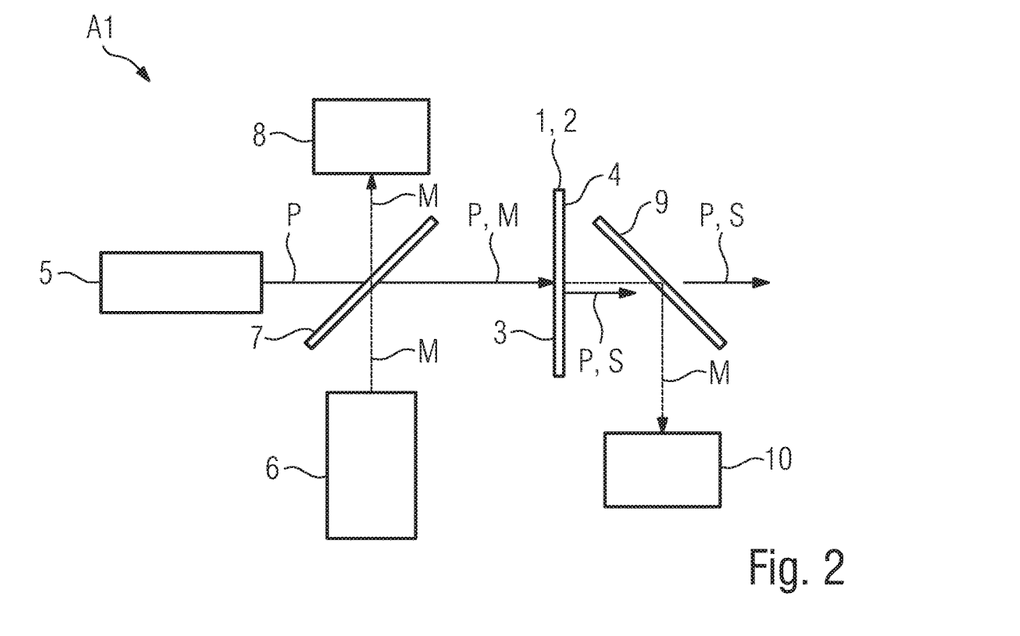
FIG. 2 shows a schematic diagram of a lighting device in accordance with a first embodiment.

FIG. 2 shows a schematic diagram of a lighting device A1 in accordance with a first embodiment. The lighting device A1 may be e.g. a vehicle headlight or a part of a vehicle headlight (e.g. a module).

The lighting device A1 includes the phosphor lamina 1 and the measurement light filter 2 attached thereto. The phosphor lamina 1 is irradiated at its first flat side 3 by primary light P originating from a primary light semiconductor light source 5. The primary light semiconductor light source 5 may include, e.g. one or a plurality of lasers and/or light emitting diodes. An optical unit for beam shaping (not illustrated) may be disposed optically downstream of the primary light semiconductor light source 5. The mixed light P, S serving as useful light is emitted at the other flat side 4 of the phosphor lamina 1 and through the measurement light filter 2. The lighting device A1 thus includes a transmissive arrangement in relation to the primary light P and the useful light P, S. The mixed light P, S may pass e.g. through a coupling-out optical unit (not illustrated).

Moreover, the lighting device A1 includes a measurement light generating arrangement in the form of a measurement light semiconductor light source 6. The measurement light semiconductor light source 6 may include one or a plurality of lasers and/or light emitting diodes. An optical unit for beam shaping (not illustrated) may be disposed optically downstream of the primary light semiconductor light source 5. The measurement light semiconductor light source 6 generates measurement light M in a spectral range disjoint from the primary light P and the secondary light S, namely here in the form of IR light. The measurement light M is transmitted, e.g. deflected, via a beam splitter 7, which is effective for the measurement light M (but e.g. not for the primary light P and for the secondary light S) partly onto the first flat side 3 of the phosphor lamina 1. The beam splitter 7 may be e.g. a partly transmissive mirror. The measurement light M passes through the phosphor lamina 1 acting as a scattering body, but is blocked, e.g. reflected or absorbed, by the measurement light filter 2 in the undamaged state, e.g. with a transmittance of less than 10%.

The other part of the measurement light M is directed or transmitted by the beam splitter 7 into a ("reference") measurement light detector 8, which is sensitive only to the measurement light M, but neither to the primary light P nor to the secondary light S. The reference measurement light detector 8 can therefore be irradiated directly by means of the measurement light semiconductor light source 6. By means of the reference measurement light detector 8, e.g. intensity fluctuations of the measurement light M emitted by the measurement light semiconductor light source 6 may be detected directly and used e.g. as a reference.

By contrast, if the phosphor lamina 1 and the measurement light filter 2 are damaged in the region of the primary light irradiation surface Fp, it is possible—as also described in FIG. 1—for the primary light P and the measurement light M to pass through directly, and thus also without being scattered. The primary light P and the measurement light M impinge, downstream of the measurement light filter 2, on a dichroic mirror 9, which transmits the primary light P and the secondary light S but reflects the measurement light M onto a (main) measurement light detector 10, which is sensitive only to the measurement light M, but neither to the primary light P nor to the secondary light S. The measurement light filter 2 is thus arranged optically between the measurement light semiconductor light source 6 and the measurement light detector 10. In various embodiments, the measurement light semiconductor light source 6 and the measurement light detector 10 are situated in a transmissive arrangement with respect to the measurement light filter 2. The main measurement light detector 10 and the reference measurement light detector 8 may be detectors of the same type.

An evaluation unit (not illustrated) coupled to the main measurement light detector 10 and to the optional reference measurement light detector 8 may evaluate a measurement signal of the measurement light detector 10. In this regard, damage may be identified e.g. by a rise in the measurement signal recorded at the main measurement light detector 10. The evaluation may be performed e.g. taking account of a measurement signal of the reference measurement light detector 8. The measurement signal of the reference measurement light detector 8 may serve e.g. for normalization or compensation of the measurement signal of the main measurement light detector 10, e.g. in order to compensate for fluctuations and/or temperature-dictated changes of the luminous flux of the measurement light M that is emitted by the measurement light semiconductor light source 6, and thus to achieve a particularly high accuracy when ascertaining damage.

In order to increase the identification accuracy further—for example for discrimination relative to disturbing ambient light in the detection spectrum of the main measurement light detector 10—the measurement light M may be pulsed and/or have a superimposed modulation frequency.

In order to ensure a high signal-to-noise ratio of the main measurement light detector 10, it may be advantageous to provide the latter with a filter (not illustrated) which transmits only the radiation of the measurement light M and otherwise blocks the useful light P, S and further extraneous light.

However, the reference measurement light detector 8 may also be dispensed with, in principle. This can be implemented in practice, for example, if a small but measurable proportion of the measurement light M passes through the measurement light filter 2, on the basis of which it is possible to check whether the measurement light semiconductor light source 6 is activated or switched on. A case of damage may be ascertained particularly simply e.g. by means of a threshold value being exceeded.

Figure 3:
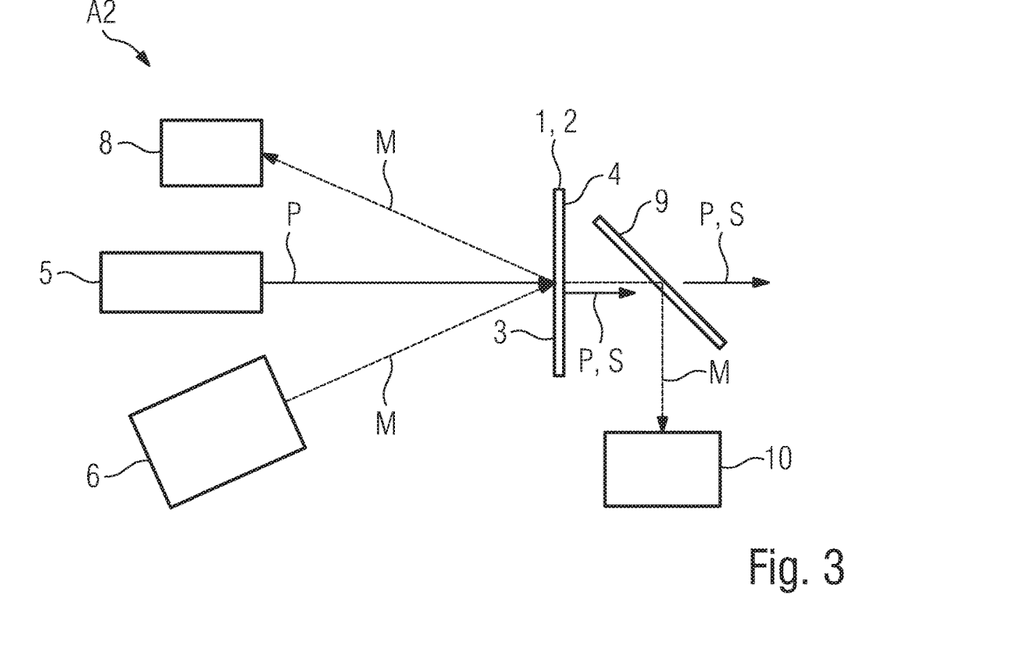
FIG. 3 shows a schematic diagram of a lighting device in accordance with a second embodiment.

FIG. 3 shows a schematic diagram of a lighting device A2. The lighting device A2 differs from the lighting device A1 in that the reference measurement light detector 8 is directed directly at the measurement light irradiation surface Fm or the primary light irradiation surface Fp. As a result, the beam splitter 7 may be dispensed with.

In this case, the measurement light filter 2 is designed to be reflective. The reference measurement light detector 8 can thus measure the measurement light M scattered by the phosphor lamina 1 and/or the measurement light M reflected by the measurement light filter 2. For a high luminous flux of the measurement light M into the reference measurement light detector 8, the measurement light semiconductor light source 6 is aligned (e.g. angled relative to the measurement light filter 2) such that its non-scattered optical path passes via the measurement light filter 2 directly into the reference measurement light detector 8.

In the case of damage, the luminous flux of the measurement light M that is incident in the main measurement light detector 10 increases, while the luminous flux of the measurement light M that is incident in the reference measurement light detector 8 decreases. However, here as well the reference measurement light detector 8 may be dispensed with, in principle.

In one variant, the reference measurement light detector 8 may be dispensed with and the main measurement light detector 10 then arranged there may be used instead of the reference measurement light detector 8. In this variant, the measurement light semiconductor light source 6 and the measurement light detector 10 are situated in a reflective arrangement in relation to the measurement light filter 2. This may be tantamount to dispensing with the main measurement light detector 10 and using the reference measurement light detector 8 instead of the measurement light detector 10. The case of damage may be ascertained by the fact that the luminous flux of the measurement light M that is reflected into the measurement light detector 10 decreases.

In another variant of the lighting device A1 and of the lighting device A2, the measurement light semiconductor light source 6—and also the beam splitter 7 in the case of the lighting device A1—may be dispensed with if the phosphor lamina 1 is also configured to convert the primary light P into the measurement light M. This may be achieved e.g. by a suitable doping of the phosphor lamina 1, by providing so-called "quantum dots", etc. Alternatively, a phosphor layer (not illustrated) for converting the primary light P and/or the secondary light S into the measurement light M may be situated between the phosphor lamina 1 and the measurement light filter 2.

The main measurement light detector 10 and—if present—the reference measurement light detector 8 may then be directed directly at the phosphor lamina 1. In the case of a transmissive arrangement of the main measurement light detector 10, in the case of damage the luminous flux of the measurement light M that is incident thereon increases, while the luminous flux of the measurement light M that is incident in the reference measurement light detector 8 decreases. In the case of a reflective arrangement of the main measurement light detector 10, the luminous flux of the measurement light M that is incident therein decreases in the case of damage.

Figure 4:
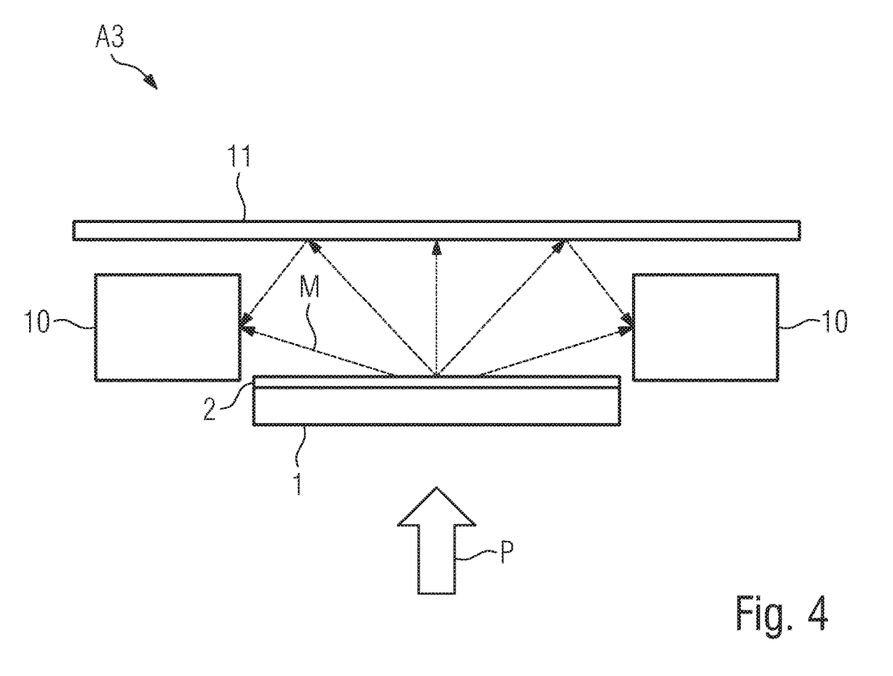
FIG. 4 shows a schematic diagram of a lighting device in accordance with a third embodiment.

FIG. 4 shows a schematic diagram of a lighting device A3 in accordance with a third embodiment. Downstream of the measurement light filter 2, only the path of the measurement light M is shown in this case. The primary light P and the secondary light S may be generated for example in accordance with an arrangement analogously to the lighting devices A1 or A2.

In the case of the lighting device A3, use is not made of a measurement light detector 8 or 10 situated optically upstream of or in reflective arrangement with the measurement light filter 2. In various embodiments, the reference measurement light detector 8 may be dispensed with. Rather, at least one main measurement light detector 10 is situated downstream of the measurement light filter 2 and the measurement light filter 2 may be situated in the field of view thereof. In this case, therefore, measurement light M may be incident directly from the measurement light filter 2 into the at least one measurement light detector 10. For this purpose, a further measurement light filter 11 is provided optically downstream of the measurement light filter 2 and at a distance therefrom, which further measurement light filter is transmissive for the primary light P and the secondary light S but is designed to be reflective for the measurement light M. The further measurement light filter 11 may be e.g. a dichroic mirror, e.g. in the form of a suitably coated cover glass. As a result, the measurement light M that has passed into the at least one measurement light detector 10 gains in intensity in comparison with only the direct incidence.

A further case of damage, namely mechanical destruction of the phosphor lamina 1 by penetration of a foreign body, would also lead to the destruction of the further measurement light filter 11. On the part of the measurement light detector 10, this leads to a rise in the power of the measurement light M from the measurement light generating arrangement also as a result of light incidence from the surroundings. In order to identify this second case of damage, with the use of the measurement light M returned or reflected from the phosphor lamina 1 on the excitation side, the reduction of said measurement light may be detected as damage to the phosphor lamina 1. For this purpose, it is possible to provide e.g. a reference measurement light detector 8 on the excitation side, e.g. analogously to the arrangement for the reference measurement light detector 8 as shown in FIG. 3.

The lighting device A3 affords the effect that the measurement light M is detectable without an additional optical system.

Although the invention has been more specifically illustrated and described in detail by means of the embodiments shown, nevertheless the invention is not restricted thereto and other variations may be derived therefrom by the person skilled in the art without departing from the scope of protection of the invention.

In this regard, instead of a ceramic phosphor lamina, it is also possible to use a body which e.g. is in sheet form or laminar and in which phosphor powder is potted in a matrix composed of light-transmissive material.

Generally, "a(n)", "one", etc. may be understood to mean a singular or a plural, in particular in the sense of "at least one" or "one or a plurality", etc., as long as this is not explicitly excluded, e.g. by the expression "exactly one", etc.

LIST OF REFERENCE SIGNS

Phosphor lamina 1
Measurement light filter 2
First flat side of the phosphor lamina 3
Second flat side of the phosphor lamina 4
Primary light semiconductor light source 5
Measurement light semiconductor light source 6
Beam splitter 7
Reference measurement light detector 8
Dichroic mirror 9
Measurement light detector 10
Further measurement light filter 11
Lighting device A1
Lighting device A2
Lighting device A3
Thickness of the phosphor lamina d1
Thickness of the measurement light filter d2
Measurement light irradiation surface Fm
Primary light irradiation surface Fp
Measurement light M
Primary light P
Secondary light S While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A lighting device, comprising:
a phosphor volume for at least partial wavelength conversion of primary light into secondary light;
a primary light semiconductor light source for irradiating the phosphor volume with primary light;
a measurement light generating arrangement for generating measurement light having a spectral composition outside the primary light and the secondary light;
a measurement light detector sensitive to the measurement light; and
a measurement light filter, which is fixedly connected to the phosphor volume and is optically arranged between the measurement light generating arrangement and the measurement light detector.

2. The lighting device of claim 1,
wherein the measurement light filter is a filter layer applied to the phosphor volume.

3. The lighting device of claim 1,
wherein a thickness of the measurement light filter is at least five times smaller than a thickness of the phosphor volume.

4. The lighting device of claim 1,
wherein the measurement light filter has been produced on the phosphor volume.

5. The lighting device of claim 1,
wherein the phosphor volume is a laminar ceramic phosphor body.

6. The lighting device of claim 1,
wherein the measurement light filter is a filter that reflects the measurement light.

7. The lighting device of claim 1,
wherein the measurement light filter is a filter that absorbs the measurement light.

8. The lighting device of claim 1,
wherein the measurement light generating arrangement comprises at least one measurement light semiconductor light source.

9. The lighting device of claim 1,
wherein the measurement light generating arrangement comprises
  the phosphor volume, which is additionally designed for converting at least one of the primary light or the secondary light into the measurement light, or
  a phosphor layer present between the phosphor volume and the measurement light filter.

10. The lighting device of claim 1,
wherein the measurement light is at least one of pulsed or modulated measurement light.

11. The lighting device of claim 1,
wherein the measurement light generating arrangement and the measurement light detector are situated in a transmissive arrangement with respect to the measurement light filter.

12. The lighting device of claim 1,
wherein an additional reference measurement light detector is irradiatable directly by means of the measurement light semiconductor light source.

13. The lighting device of claim 1,
wherein the measurement light generating arrangement and the measurement light detector are situated in a reflective arrangement with respect to the measurement light filter.

14. The lighting device of claim 1,
wherein the lighting device is designed as a vehicle illumination device.

15. A headlight, comprising:
at least one lighting device, comprising:
  a phosphor volume for at least partial wavelength conversion of primary light into secondary light;
  a primary light semiconductor light source for irradiating the phosphor volume with primary light;
  a measurement light generating arrangement for generating measurement light having a spectral composition outside the primary light and the secondary light;
  a measurement light detector sensitive to the measurement light; and
  a measurement light filter, which is fixedly connected to the phosphor volume and is optically arranged between the measurement light generating arrangement and the measurement light detector.

* * * * *